(12) United States Patent
Verkaar et al.

(10) Patent No.: US 9,332,764 B2
(45) Date of Patent: May 10, 2016

(54) AQUEOUS COMPOSITION FOR INACTIVATING SPORULATED AND/OR NON-SPORULATED COCCIDIAN PARASITES

(75) Inventors: Edward Verkaar, LW Baarlo (NL); Ludger Grunwald, Wuppertal (DE); Stefan Kuepper, Langenfeld (DE)

(73) Assignee: Ecolab USA Inc., St. Paul, MN (US)

( * ) Notice: Subject to any disclaimer, the term of this patent is extended or adjusted under 35 U.S.C. 154(b) by 1056 days.

(21) Appl. No.: 12/671,880

(22) PCT Filed: Aug. 16, 2007

(86) PCT No.: PCT/EP2007/058530
§ 371 (c)(1),
(2), (4) Date: Jun. 21, 2011

(87) PCT Pub. No.: WO2009/021557
PCT Pub. Date: Feb. 19, 2009

(65) Prior Publication Data
US 2011/0250295 A1    Oct. 13, 2011

(51) Int. Cl.
*A01N 59/00* (2006.01)
*A01N 25/30* (2006.01)
*A01N 41/04* (2006.01)

(52) U.S. Cl.
CPC .............. *A01N 59/00* (2013.01); *A01N 25/30* (2013.01); *A01N 41/04* (2013.01)

(58) Field of Classification Search
CPC ....... A01N 59/00; A01N 25/30; A01N 41/04; A01N 2300/00
See application file for complete search history.

(56) References Cited

U.S. PATENT DOCUMENTS

| | | | | |
|---|---|---|---|---|
| 3,967,039 A | * | 6/1976 | Ninane et al. | 428/403 |
| 4,963,287 A | | 10/1990 | Hutchings | |
| 5,280,042 A | * | 1/1994 | Lopes | 514/557 |
| 5,358,045 A | * | 10/1994 | Sevigny et al. | 166/270.1 |
| 2010/0055196 A1 | | 3/2010 | MacGregor | |

FOREIGN PATENT DOCUMENTS

| | | |
|---|---|---|
| GB | 2108389 | 5/1983 |
| JP | 2004-210726 A * | 7/2004 |
| JP | 2004210726 | 7/2004 |
| WO | WO02/091832 | 11/2002 |

OTHER PUBLICATIONS

Dow Product Safety Assessment: DOWFAX Anionic Surfactants, obtained from the web at http://msdssearch.dow.com/PublishedLiteratureDOWCOM/dh_07ec/0901b803807ecd28.pdf?filepath=productsafety/pdfs/noreg/233-00307.pdf&fromPage=GetDoc on Jul. 9, 2015.*

* cited by examiner

*Primary Examiner* — John Pak
*Assistant Examiner* — Nathan W Schlientz
(74) *Attorney, Agent, or Firm* — Merchant & Gould P.C.

(57) ABSTRACT

The invention relates to an aqueous composition for inactivating sporulated and/or non-sporulated Coccidia parasites comprising 15 to 115 ppm chlorine dioxide and 0.01 to 1 wt-% of an anionic surfactant having one or more $C_6$ to $C_{18}$ alkyl groups and one or more aryl groups. The invention further relates to a method for preparing the composition and to a method for inactivating sporulated and/or non-sporulated Coccidia by applying the composition.

16 Claims, No Drawings

AQUEOUS COMPOSITION FOR INACTIVATING SPORULATED AND/OR NON-SPORULATED COCCIDIAN PARASITES

The technical field of the present invention relates to an aqueous composition for inactivating sporulated and/or non-sporulated Coccidian parasites. A further object of the present invention is a method for preparing the aqueous composition, and a method for inactivating sporulated and/or non-sporulated Coccidia by applying the composition.

Coccidia are spore-forming parasites which infect the intestinal tracts of animals. Coccidia are obligate intracellular parasites which means that they must live and reproduce within an animal cell.

The disease caused by the Coccidian infection is named Coccidiosis. This is a parasitic disease which spreads from animal to animal by contact with infected faeces. The primary symptom of the disease is diarrhoea which is bloody in severe cases. Older infected animals are asymptomatic, which means that they show no symptoms of the disease. However, young or immunocompromised animals may suffer from severe symptoms including death.

Coccidia can infect a wide variety of animals including humans and livestock.

Coccidiosis can be regarded as a primary parasitic disease with significant economic impacts on the production of poultry, pork, and beef. These economic impacts result from the fact that a prophylactic in-feed medication is necessary to avoid spreading of Coccidiosis in livestock. If prophylactic medication fails and feed conversions are poor, the effects for an affected breeder are detrimental. For the prophylactic in-feed medication coccidiostats or vaccines are currently used. However, it is also known that the Coccidian parasites become increasingly resistant to these products.

The Coccidiae comprise among others the families Eimeriidae and Lankesterellidae. The Coccidians responsible for disease in livestock are *Eimeria*, *Tyzzeria*, and *Isospora*; all genera of the Coccidia. These orders also comprise other human disease-causing pathogens (*Cyclospora*, *Cryptosporidium* and *Toxoplasma*). Avian Coccidiosis is primarily caused by the *Eimeria* species: *Eimeria tenella, necatrix, macima, brunetti, acervulina, mivati, praecox,* and *mitis* cause Coccodiose in chickens (broiler breeders), *Eimeria anatis* and *danailovi* cause disease in ducks, *Eimeria adenoides, gallopavoris, meleagridis, meleagrimitis* cause disease in turkeys. There are many other *Eimeria* species specifically responsible for disease in other avians (geese, pheasants, partridges and other). *Eimeria* species are found and cause disease in pigs (*Eimeria debliechi*) and bovines (*Eimeria bovis, zuernii,* and *ellipsoidalis*).

In all mentioned host species, clinical symptoms may vary. Pathogenicity is dependent on host physical condition, age, and immune status. Within a host, levels of pathogenicity may vary per *Eimeria* species. Within broilers, weaning pigs and calves, clinical signs are predominantly loss of performance and FCR (food conversion ratio). *Eimeria* cause necrotic inflammations of the gut leading to caecal damage with bloody droppings, gut damage or death: Again, the level of enteritis may vary within species range. *Eimeria tenella* causes severe caecal damage in broilers with bloody droppings. *Eimeria acervulina* causes gut damage which may lead to mortality through necrotic enteritis in broilers. *Eimeria necatrix* causes sudden death in broiler breeders etc.

Avian *Eimeria* are committed parasites with complex life cycles. Generally, oocysts (eggs) undergo sporogeny in the environment, 24 hours after littering. The oocysts contain four sporocysts, which contain two sporozoites. Maturation into full sporozoites will occur after ingestion within the gut lumen after ingestion of litter-contaminated water or feed. The process of maturation within the gut is enhanced by trypsin, bile, and $CO_2$. The sporozoites enter, depending on the species, gut epithelial or gut crypt epithelial cells for further intracellular maturation. Within host cells, sporozoites undergo asexual reproduction (schizogeny) resulting in merozoites, which break free from the cell and infect other gut cells. Merozoites enter cells and differentiate into male (microgamonts) or female (macrogamonts) organisms. The macrogamonts break free from infected cells as oocysts, which can be fertilised in the gut lumen and subsequently exit the lumen, which effectively restarts the *Eimeria* life cycle. Prelatent periods may range from 4 to 5 days postinfection. Maximum oocyst output ranges from 6 to 9 days postinfection. The necrotic enteric effects are only partially caused by the protozoic parasite. Sporozoites and Merozoites may be regarded as inoculating needles causing other possible pathogenic and non-pathogenic bacteria (*Salmonella pullorum, Staphylococcus albus, Escherichia coli* a. o.) to penetrate the tissue of the caecal gut and enter the blood and lymphoid organs causing septicaemia and inflammation of organs.

Although Coccidia are host-specific and not all Coccidia cause gastroenteric disease (diarrhoea, bloody stools, reduced FCR, poor egg production), it remains a highly contagious organism affecting livestock kept in warm, narrow and humid environments. Mainly depending on the immune status and host specificity, Coccidia can affect livestock: poultry, pigs, rabbits, humans, and even fish. Coccidiosis in poultry is a major threat while Coccidiosis in intensive swine production is increasing. In broilers, turkeys, and periodic replacements in feed coccidiostats prevent clinical disease. A strong drawback of these coccidiostats is the toxicity for both animals and humans. Coccidiostats cause loss of performance (weight loss, egg production) and reduced feed conversion, ultimately resulting in an economic loss. The residues may also present a possible health hazard for humans, therefore a strict control regime on dosage and withdrawal periods need to be strictly implemented.

A second drawback is drug resistance when using anticoccidials, and organism specificity which is a problem when multiple species have invaded the gut. These drugs can be classified into two classes: First are the chemicals that alter or influence the metabolism of the parasites such as amprolium, clopidol a. o. Second are the polyether ionophores that alter ion transport via the cell membrane or disrupt osmotic balance such as monensin, salinomycin a. o. Due to problems of drug resistance, shuttle and rotation programmes are used. In broiler breeders, live attenuated vaccines are given via the drinking water at 7-10 days of age. As with chemotherapeuticals, the use of vaccines have drawbacks too. A uniform dosage may under- or overdose animals which in the latter case may cause disease when a virulent type is used. Moreover, use of live attenuated vaccines cause subclinical infections and shedding of oocysts in the environment. Some farmers use coccidiocidal water treatment at peak challenge age. As oocysts are durable (under favourable conditions, they can survive for two years) and will persist in the environment longer than e.g. viruses, complete challenge eradication may be impossible. This is not necessary as log 2-log 3 or more oocysts are required to cause mild symptoms. However, reducing challenge dose is beneficial for increasing immunity and decreasing signs of disease.

A Coccidial infection causes flock immunity which is well understood in agriculture. However, every Coccidian species has its own specificity and antigenic properties: As with many other protozoan pathogens, *Eimeria* is capable of swiftly altering antigenic and/or genetic properties therefore causing major genetic heterogeneities. These properties are an inherent feature for survival. Another issue is the durability of the oocysts. Most disinfectants are rendered useless due to the oocyst structure. The walls of the oocyst consist of a dense, 10 nm outer layer and 90 nm inner layer. The former constitutes 25% of the total wall mass and contains bipolar organic molecules (fatty acids, fatty alcohols, phospholipids) and cholesterol as a fluid stabiliser. The structure of the outer cell layer allows passage of only small uncharged molecules. The inner layer is mainly composed of high molecular glycoproteins resulting in an overall impenetrable, highly sturdy membrane. The protective outer layer effectively prevents penetration of larger and/or charged molecules therefore most liquid disinfectants will not be effective.

The last, probably best method of coccoid eradication is in-house management, which is primarily based on prevention. Oocysts are transmitted via litter. Thus, good litter management helps to reduce a coccoid challenge. Because Coccidial oocysts are ubiquitous in any farm environment and have such a large reproduction potential, it is difficult to keep animals Coccidia-free. Oocysts sporulate readily, but their viability is reduced within 3 weeks by high levels of ammonia. Basically, farmers remove caked litter and let the house air out for 3 weeks and subsequently dress new oocyst-free litter before introducing a new flock. A thorough cleanout between flocks, changing clothes between houses and other hygienic measures further decrease the possibility of coccoid infestation.

Full challenge eradication may be impossible and not desirable for enhancing flock immunity. Large doses of *Eimeria* oocysts are mandatory (100-1000) in causing clinical manifestations. Furthermore, coccoid oocysts are sturdy and resist most disinfectants. A study has shown the following chemicals to be ineffective and thus unsuited for eradication: peracetic acid, formaldehyde, potassium hydroxide, sulfuric acid, potassium dichromate, potassium iodide, formalin, iodophors, cresylic acid, sodium hypochlorite, benzalkonium chloride, glutaraldehyde, phenolic substances, quaternary ammonium compounds, and copper sulfate.

U.S. Pat. No. 5,985,875 describes 1,2,4-triazine-3,5-dione derivatives, their production, and use for inactivating parasitic protozoa such as Coccidia.

JP 2004-210726 describes the use of chlorine-based chemicals like chlorine dioxide in the presence of a sodium citrate phosphoric acid buffer solution for the inactivation of Coccidia. The document describes to use chlorine dioxide in concentrations between 100 and 6,400 ppm, preferably 200 to 800 ppm.

Chlorine dioxide is a very reactive and toxic gas. The toxicity results from the strong oxidative power of the compound and from the fact that the compound releases chlorine and oxygen when it reacts. The maximum concentration of gaseous chlorine dioxide gas in any working environment is according to the definition of the German Research Foundation not higher than 0.1 ppm.

Therefore the disadvantage of the method described in JP 2004-210726 is that high concentrations of chlorine dioxide have to be used in order to sufficiently inactivate the Coccidian parasites. The inventors of the present invention have performed experiments to lower the limit of the concentration of chlorine dioxide in a solution which is still effective, inactivating Coccidian parasites. It was found that concentrations below 120 ppm chlorine dioxide are ineffective to eradicate coccoid organisms.

Therefore the technical object of the present invention was to provide a composition for the inactivation of Coccidian parasites which comprises less chlorine dioxide and is therefore less toxic to the animals and user.

The technical object of the present invention is solved by an aqueous composition for inactivating sporulated and non-sporulated Coccidian parasites comprising 15 to 115 ppm chlorine dioxide and 0.01 to 1 wt. % of an anionic surfactant having one or more $C_6$-$C_{18}$ alkyl groups and one or more aryl groups.

The inventors of the present invention have surprisingly found that, when mixing an aqueous solution comprising chlorine dioxide with an anionic surfactant having one or more $C_6$-$C_{18}$ alkyl groups and one or more aryl groups this solution is able to inactivate sporulated and/or non-sporulated Coccidian parasites even if the chlorine dioxide concentration is below 120 ppm in the solution.

This result could not be expected because it was known that only higher concentrations of chlorine dioxide above 200 ppm and preferably around 800 ppm would completely inactivate sporulated and/or non-sporulated Coccidian parasites. The experiments of the inventors show that chlorine dioxide alone will not inactivate if the concentration of chlorine dioxide in the solution is below 120 ppm.

In addition the inventors have also investigated whether combinations of chlorine dioxide with other surfactants like for example alkyl sulfonates, amine oxides, ethoxylated polyalcohols, quaternary ammonium compounds, lauryl hydroxy sulfane, and alkyl ether sulfates have an effect in combination with lower concentrations of chlorine dioxide. However, in these cases it is found that the sporulated and/or non-sporulated Coccidian parasites can not be inactivated.

In a preferred embodiment the aqueous composition according to the invention comprises 20 to 100 ppm chlorine dioxide, more preferably 25 to 50 ppm chlorine dioxide.

It is furthermore preferred that the composition comprises 0.05 to 0.5 wt. %, preferably 0.1 to 0.3 wt. % of the surfactant.

In a further preferred embodiment the anionic surfactant is a sulfonate surfactant having one or more $C_6$-$C_{18}$ alkyl groups and one or more phenyl groups. Examples for these sulfonates are for instance alkyl aryl sulfonates, sulfur succinates, and isethionates. As alkyl aryl sulfonates cumene sulfonates, xylene sulfonates, naphtyl sulfonates, and alkyl benzene sulfonates can be used which are substituted with one or more $C_6$-$C_{18}$ alkyl groups.

In the most preferred embodiment the anionic surfactant is a $C_6$-$C_{18}$ alkyl diphenyl oxide disulfonate and/or an alkyl (sufophenoxy)benzene sulfonate.

The composition according to the invention is applied to a Coccidia contaminated surface for 1 minute to 1 hour, preferably 15 minutes to 45 minutes. The composition is preferably applied by spraying onto the contaminated surface.

In a further preferred embodiment the composition according to the invention can be applied in the form of a foam so that the user is able to see the surface where the composition is applied. In another preferred embodiment the composition is coloured for the same purpose, namely also the identification of the surface where the solution was applied.

Furthermore the invention also relates to a method for preparing the aqueous composition according to the invention. This is done by combining a chlorite part comprising alkali metal chlorite and as a second part an acid solution comprising 1 to 5 wt. %, preferably 1.5 to 3 wt. % of a weak carboxylic acid, 2 to 10 wt. %, preferably 3 to 8 wt. %, and more preferred 4 to 7 wt. % of phosphoric acid, and 10 to 25 wt. %, preferably 13 to 20 wt. %, and most preferred 15 to 18 wt. % of an anionic surfactant having one or more $C_6$-$C_{18}$ alkyl groups and one or more phenyl groups, and dilution of the mixture with water.

In a preferred embodiment the anionic surfactant can be added separately to the chlorite part and the acid solution.

The chlorite part comprising the alkali metal chlorite, which is preferably a sodium chlorite, can be an aqueous solution comprising 2 to 15 wt. % alkali metal chlorite, preferably 5 to 10 wt. % alkali metal chlorite.

The chlorite part can also be a solid comprising alkali metal chlorite and a filler. The filler is preferably sodium carbonate. If the chlorite part is a solid part it can be in the form of a tablet, a granule, or a powder.

The acid solution comprises a weak carboxylic acid which is selected from the group consisting of acetic acid, citric acid, lactic acid, glycolic acid, tartaric acid, and propionic acid and mixtures thereof.

Furthermore the acid solution comprises phosphoric acid. The combination of a weak carboxylic acid and a phosphoric acid is necessary to release the chlorine dioxide continuously and slowly by reaction of the alkali metal chlorite with the acids.

Furthermore the acid solution can comprise the anionic surfactant having one or more $C_6$-$C_{18}$ alkyl groups and one or more phenyl groups. This anionic surfactant is preferably a sulfonate surfactant, more preferred an aromatic sulfonate surfactant, and most preferred a $C_6$-$C_{18}$ alkyl diphenyl oxide disulfonate and/or a $C_6$-$C_{18}$ alkyl(sulfophenoxy)benzene sulfonate.

The composition which is made by combining the chlorite part and the acid solution is furthermore diluted with water to prepare the aqueous use solution for inactivating sporulated/ and or non-sporulated Coccidian parasites. The dilution is carried out in a ratio of 1:10 to 1:1000, preferably 1:50 to 1:500.

The aqueous composition according to the invention can also be prepared with other methods like for example other chlorine dioxide releasing compounds or chlorine dioxide releasing electrolysis in which an electrical current within a cassette in which sodium chlorite solution flows will release chlorine dioxide in an aqueous environment.

The acid solution and/or the solution comprising the anionic surfactant can furthermore comprise additives like thickeners, solubilising agents, and buffering agents. However, it is important that these additives are carefully selected so that they do not react with the chlorite part of the solution after mixing of the chlorite part and the acidic part of the solution.

The following examples are provided to further illustrate the invention.

EXAMPLES

Materials and Methods

For the experiments 20 g female Balb/C-mice were used. As parasite, Eimeria papillata which is a mouse-specific Coccidia, hence suitable for the purpose of this experiment is used. The flotation medium was prepared containing 124.5 g NaCl and 435.8 g saccharide which was diluted with water and filled up to 1 litre. Fresh non-sporulated oocysts were prepared. Subsequently the Balb/C-mice were infected with 20,000 sporulated oocysts. From the fourth day after infection, fresh mouse excrement is collected and isolated by flotation. Residual flotation medium is removed by washing three times with clean water.

Sporulated infectious oocysts were incubated at 25° C. for one week. After complete sporulation the oocysts may be further used for infection or they can also be stored at 4° C. in a 2% solution of potassium dichromate.

A chlorine dioxide solution is prepared by mixing a solution containing sodium chlorite and an acidic solution. By reaction chlorine dioxide is produced. The solution comprises 120 ppm chorine dioxide. By further dilution, chlorine dioxide solutions of 40, 20, 10, 4, 1, and 0.5 ppm are produced which are immediately used for the experiments.

Example 1

Incubation of Fresh Non-Sporulated Oocysts in a Chlorine Dioxide Comprising Solution Oocysts of Eimeria papillata were filtered from fresh mice excrements and incubated for 60 min with freshly produced chlorine dioxide solution at concentrations of 40, 20, 10, 4, 1, 0.5 ppm at room temperature. After 60 min incubation time the oocyst suspensions were washed with water and cultured for sporulation in 1 ml water. The probes were incubated for one week at 25° C. As control a non-treated, non-sporulated oocyst sample was used which was also incubated for one week at 25° C. After seven days it was checked if a sporulation occurred. (see table 1)

TABLE 1

| No. | $ClO_2$ concentration | incubation time | result |
|---|---|---|---|
| 1 | none, control | — | complete sporulation |
| 2 | 40 ppm | 60 min | partial sporulation |
| 3 | 20 ppm | 60 min | complete sporulation |
| 4 | 10 ppm | 60 min | complete sporulation |
| 5 | 4 ppm | 60 min | complete sporulation |
| 6 | 1 ppm | 60 min | complete sporulation |
| 7 | 0.5 ppm | 60 min | complete sporulation |

The results of the experiment show that at concentrations below 40 ppm a complete or partial sporulation occurred. This means that a complete inactivation of the Coccidia is not possible with chlorine dioxide only at concentrations of less than 40 ppm at an incubation time of 60 min. The control example shows that a complete sporulation occurred for the non-treated sample.

In the same way experiments were carried out with the aqueous composition according to the invention comprising chlorine dioxide and as an anionic surfactant Dofax 2A1 (Dow Chemicals) which is a mixture of a disodium oxybis (dodecyl benzenesulfonate) and a dodecyl(sulfophenoxy)disodium salt of benzene sulfonic acid. The composition comprises between 0.5 to 25 ppm chlorine dioxide and 0.2 wt. % of the anionic surfactant. (see table 2)

TABLE 2

| No. | $ClO_2$ concentration | incubation time | result |
|---|---|---|---|
| 1 | none, control | — | complete sporulation |
| 2 | 25 ppm | 60 min | no sporulation |
| 3 | 20 ppm | 60 min | no sporulation |
| 4 | 10 ppm | 60 min | partial sporulation |
| 5 | 4 ppm | 60 min | complete sporulation |
| 6 | 1 ppm | 60 min | complete |

TABLE 2-continued

| No. | ClO$_2$ concentration | incubation time | result |
|---|---|---|---|
| 7 | 0.5 ppm | 60 min | sporulation complete sporulation |

The results show that the composition according to the invention, comprising a low concentration of chlorine dioxide and the alkyl diphenyl oxide disulfonate surfactant, is effective against Coccidia at concentrations of 20 ppm and higher when an incubation time of 60 min is used. At a concentrations of 10 ppm; partial sporulation is observed while at concentrations below 4 ppm complete sporulation is observed.

It follows from these experiments that at concentrations above 15 ppm chlorine dioxide the non-sporulated oocysts of Coccidia can be completely inactivated. As a result, chlorine dioxide concentrations above 15 ppm are able to completely inactivate the oocysts Example 2

Infection with Sporulated Oocysts

A further series of experiments was performed in order to evaluate the inactivation pattern of sporulated oocysts. For this purpose 30,000 oocysts were incubated for 60 min with the chlorine dioxide-containing composition at levels varying between 4 and 40 ppm chlorine dioxide. After that the oocyst suspensions were washed with water for three times and 20,000 oocysts were orally administered to a mouse. Per concentration one mouse was used. In addition two mice were treated, each with 20,000 non-treated, sporulated oocysts for control purposes. From the fourth day after infection samples of the excrements of the mice were taken daily and the presence of oocysts of *Eimeria papillata* was examined. (see table 3)

TABLE 3

| mouse no. | concentration ClO$_2$ solution | incubation time | excretion 4 dpi | 5 dpi | 6 dpi | 7 dpi |
|---|---|---|---|---|---|---|
| 1 | -, control | — | +++ | ++ | ++ | + |
| 2 | 40 ppm | 60 min | + | + | + | + |
| 3 | 20 ppm | 60 min | ++ | ++ | + | + |
| 4 | 10 ppm | 60 min | ++ | ++ | ++ | + |
| 5 | 4 ppm | 60 min | ++ | ++ | ++ | + |
| 6 | 120 ppm | 60 min | − | − | − | − |
| 7 | 240 ppm | 60 min | − | − | − | − | dpi = days after infection
+++ massive excretion of oocysts
++ excretion of many oocysts
+ excretion of few oocysts
− no oocysts detectable The results show that with concentrations of chlorine dioxide between 4 and 40 ppm the excretion of oocysts of *Eimeria papillata* cannot be avoided in Balb/C-mice after the treatment of the oocysts with these concentrations of chlorine dioxide at incubation times of 60 min.

Trials were also performed at concentrations of 120 ppm and 240 ppm. In these tests it was discovered that no detectable oocysts could be found. At these concentrations Coccidia are effectively exterminated.

The same experiments were carried out with the aqueous composition according to the invention. A composition was used having a chlorine dioxide concentration between 4 ppm and 25 ppm and the concentration of an anionic surfactant as described in example 1. (see table 4)

TABLE 4

| mouse no. | concentration ClO$_2$ solution | incubation time | excretion 4 dpi | 5 dpi | 6 dpi | 7 dpi |
|---|---|---|---|---|---|---|
| 1 | -, control | — | +++ | ++ | ++ | + |
| 2 | 25 ppm | 60 min | − | − | − | − |
| 3 | 20 ppm | 60 min | − | − | − | − |
| 4 | 10 ppm | 60 min | ++ | ++ | ++ | + |
| 5 | 4 ppm | 60 min | ++ | ++ | ++ | + | dpi = days after infection
+++ massive excretion of oocysts
++ excretion of many oocysts
+ excretion of few oocysts
− no oocysts detectable The results in table 4 show that using the compositions described by the invention at chlorine dioxide concentrations of higher than 20 ppm the composition completely inactivates Coccidia as no oocysts are developed or detected in the mouse excrements. At concentrations below 15 ppm starting from the fourth day after infection, many oocysts are excreted. Therefore, at these concentrations, there is no complete inactivation.

The invention claimed is:

1. Aqueous composition for inactivating sporulated and/or non-sporulated Coccidia parasites comprising:
   15 to 50 ppm chlorine dioxide;
   an acid solution comprising:
     (i) 1 to 5 wt-% of a weak carboxylic acid by weight of the acid solution; and
     (ii) 2 to 10 wt-% phosphoric acid by weight of the acid solution; and
   0.01 to 1 wt-% of an anionic surfactant selected from the group consisting of C6 to C18 mono- and di-alkyl diphenyl oxide disulfonates and mixtures thereof.

2. The aqueous composition according to claim 1, wherein the composition comprises 20 to 50 ppm chlorine dioxide.

3. The aqueous composition according to claim 1, wherein the composition comprises 0.05 to 0.5 wt-% of the anionic surfactant.

4. A method for inactivating sporulated and/or non-sporulated Coccidia comprising applying the composition according to claim 1 to a Coccidia contaminated surface for 1 minute to 1 hour.

5. The method of claim 4, wherein the composition is applied to the contaminated surface for 15 minutes to 45 minutes.

6. A method for preparing an aqueous composition, the method comprising combining:
   (a) a chlorite part comprising an alkali metal chlorite;
   (b) an acid solution comprising:
     (i) 1 to 5 wt-% of a weak carboxylic acid by weight of the acid solution; and
     (ii) 2 to 10 wt-% phosphoric acid by weight of the acid solution; and
   (c) 10 to 25 wt-% of anionic surfactant selected from C6 to C18 mono- and di-alkyl diphenyl oxide disulfonates and combinations thereof; and diluting the mixture of (a), (b) and (c) with water,
   wherein the aqueous composition comprises 15 to 50 ppm chlorine dioxide and 0.01 to 1 wt-% of the anionic surfactant, and wherein the aqueous composition is effective against Coccidia parasites.

7. The method according to claim 6, wherein the chlorite part is an aqueous solution comprising 2 to 15 wt-% of an alkali metal chlorite.

8. The method according to claim 6, wherein the chlorite part is a solid comprising alkali metal chlorite and a filler.

9. The method according to claim 8, wherein the filler is sodium carbonate.

10. The method according to claim 8, wherein the chlorite part is a solid part in form of a tablet, a granule, or a powder.

11. The method according to claim 6, wherein the weak carboxylic acid is selected from the group consisting of acetic acid, citric acid, lactic acid, glycolic acid, tartaric acid, propionic acid and mixtures thereof.

12. The method according to claim 6, wherein the alkali metal chlorite is sodium chlorite.

13. An aqueous composition for inactivating sporulated and/or non-sporulated Coccidia parasites obtained by the method according to claim 6, wherein the composition is formed into a foam prior to use.

14. The method of claim 6, wherein the composition is formed into a foam prior to use.

15. The method of claim 6, wherein the composition further comprises a dye.

16. The method of claim 6, wherein the composition comprises 0.05 to 0.5 wt-% of the anionic surfactant.

* * * * *